United States Patent [19]

Weiss et al.

[11] Patent Number: 4,997,383

[45] Date of Patent: Mar. 5, 1991

[54] DENTAL IMPLANT

[75] Inventors: Charles M. Weiss, New York, N.Y.; Jack E. Lemons, Birmingham; Martha W. Bidez, Alabaster, both of Ala.

[73] Assignees: Oratronics, Inc, New York, N.Y.; U.A.B. Research Foundation, Birmingham, Ala.

[21] Appl. No.: 361,592

[22] Filed: Jun. 5, 1989

[51] Int. Cl.[5] ............................................. A61C 8/00
[52] U.S. Cl. ................................................... 433/176
[58] Field of Search ................ 433/176, 173, 174, 221

[56] References Cited

U.S. PATENT DOCUMENTS

| | | | |
|---|---|---|---|
| 3,623,226 | 11/1971 | Edelman | 433/176 |
| 3,950,850 | 4/1976 | Driskell et al. | 433/176 |
| 4,302,188 | 11/1981 | Driskell | 433/176 |
| 4,531,915 | 7/1985 | Tatum, Jr. | 423/176 |

Primary Examiner—Cary E. Stone
Attorney, Agent, or Firm—James & Franklin

[57] ABSTRACT

A dental implant is specifically designed to properly distribute the forces exerted on the bone by the implant and to foster optimum osteal and/or fibro-osteal integration of the implant with the bone, thereby to improve the quality and longevity of proper implant function. The shaping and location of various surfaces of the implant are specifically designed to minimize both under- and over-stressing of the bone which leads to failure, and to maximize the formation and advantageous functioning of a peri-implant ligament, direct bone apposition, or combinations thereof. Novel structure may be provided so that heads of different shapes and inclinations can be selectively used with the implant to meet the patient's individual physiologic requirements, while at the same time facilitating submerged healing.

29 Claims, 8 Drawing Sheets

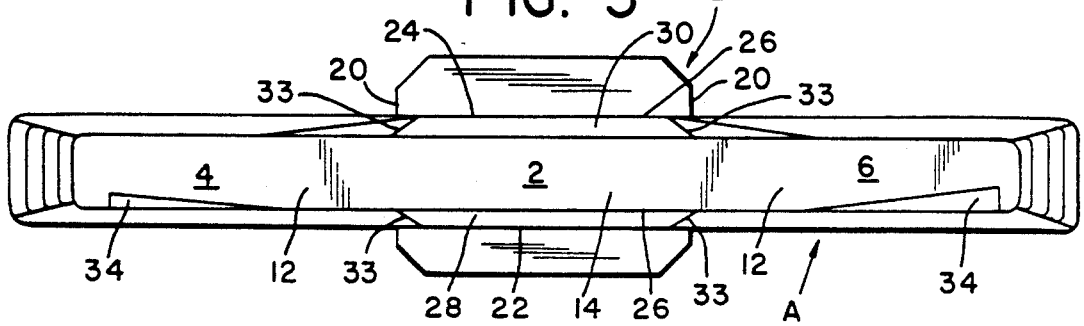
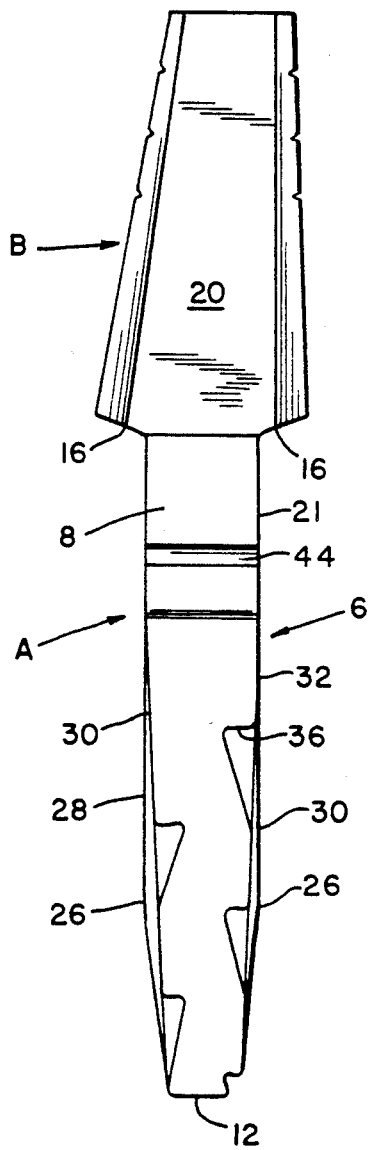
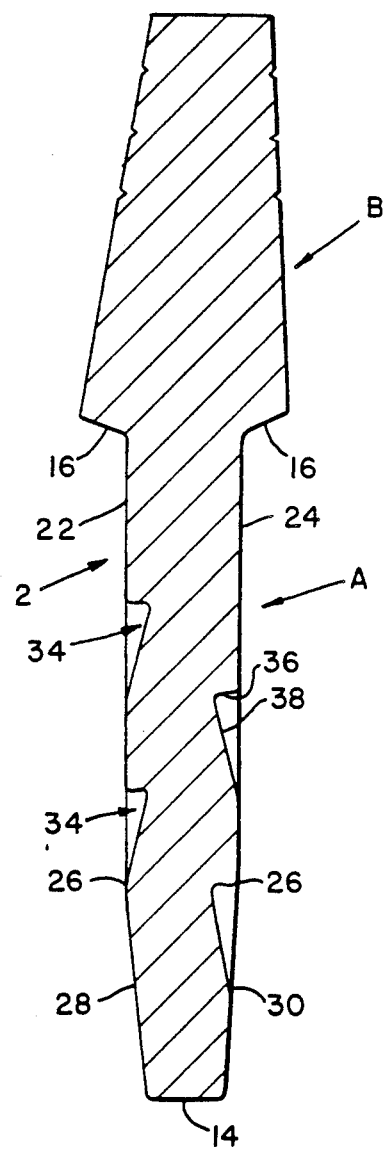

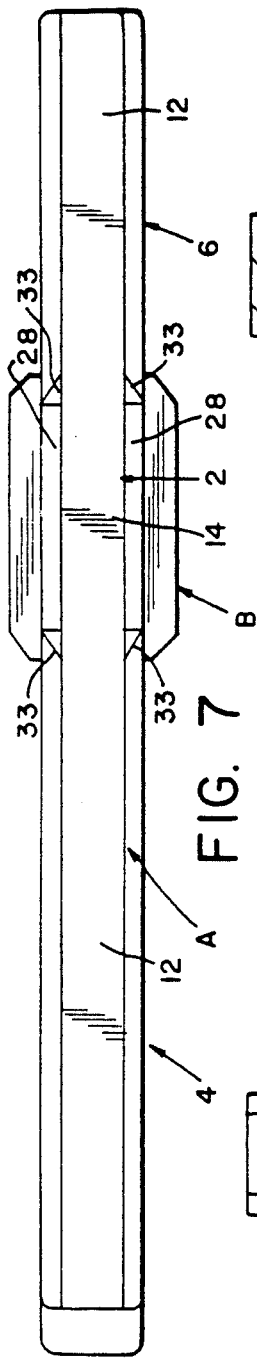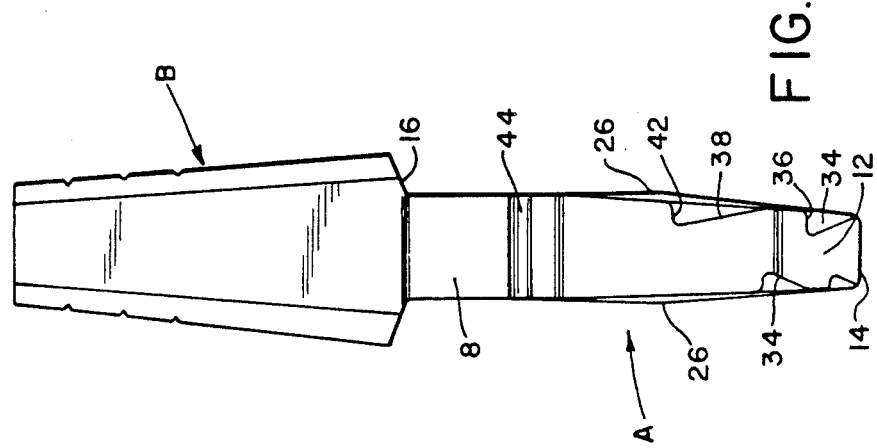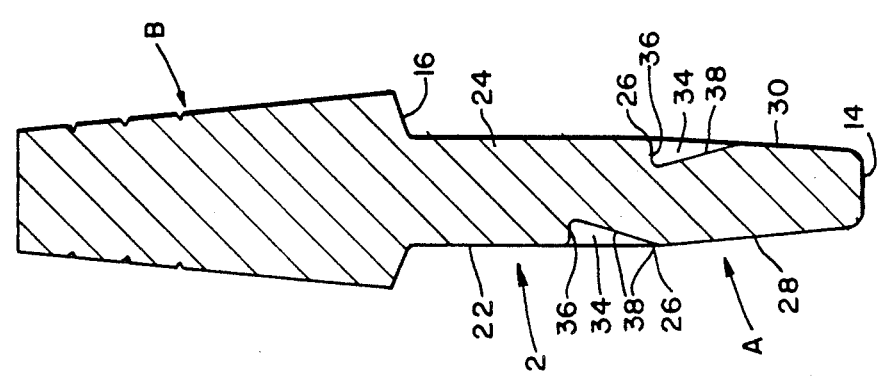

DENTAL IMPLANT

The present invention relates to improvements in the design of dental implants adapted to be inserted into the bone and to support single or multi-unit fixed or removable dental prostheses, and in particular to that type of implant which is wide and thin and to which the term "blade" is generally loosely applied.

So-called blade-type implants have been used for a considerable period of time, and with significant success, in dental prosthetics. They generally comprise a thin wide section, here called the implant portion, surmounted by an upwardly extending, usually thicker section generally called a "head". The thin wide section is inserted into a roughly correspondingly shaped opening formed in the patient's bone and the head extends beyond the patient's gum, into the oral cavity. It is to the head that prosthetic elements carrying artificial teeth are ultimately secured.

After the blade has been inserted into the bone various physiological processes occur which act to support and retain the implant in the bone, ultimately to hold the prosthetic device in position in the mouth. One such process is the growth of bone directly against the implant portion that is within the jaw, to retain and support the implant.

To achieve direct bone apposition to the implant portion within the jaw bone, aseptic, atraumatic insertion surgery folowed by afunctional healing—healing in the absence of force on the implant—is very advantageous. This is achieved through submerged healing, utilizing a removable abutment head that is fixed to the implant only at the completion of healing. A removable healing head may be used in place of the ultimate abutment head during the healing process, which healing head may be completely submerged into the gum or exposed at the surface of the gum.

Because each patient's mouth is different the heads of implants must project from the bone at different angles for each patient. To facilitate the accommodation of these individual requirements and to optimize initial osteal integration, the removable heads above referred to may be provided with different inclinations, a group of differently configured heads being available for selection therefrom. After the implant portion, without an abutment head, is inserted into the bone, preferably with a healing head thereon, and submerged for a period of time to minimize the possibility of force on the implant during healing, thereby to optimize osteal integration, the implant portion is then exposed, the healing head is removed, and the selected abutment head of appropriate inclination is inserted into a pre-formed slot in the implant, where it is retained in any appropriate manner, after which impressions and other procedures are undertaken to affix a prosthesis to the implant.

While removable abutment and healing heads in implants have been known, in the past they have been used only in connection with implant bodies of significant width, such as cylinder implants, which require that the patient have available bone areas of correspondingly greater width, thus greatly limiting the applicability of such implants as compared to implants of the blade type. Moreover, there are other aspects in which blade-type implants are superior to cylinder-type implants. Removable heads of blade-type implants have been provided where the removable heads are designed to be screwed onto an upstanding externally threaded post, but that introduces problems of fragility and makes it difficult if not impossible to achieve optimum submerged healing. Another attempt has been made to provide a blade-type implant with a removable head, but in that instance the body of the implant was widened at the area where the head was to be inserted, thus making it comparable in bone width requirement to the cylinder implants. The present invention, however, is believed to be the first time that optimum head removability and submerged healing have been achieved with a blade-type implant without increasing its maximum width.

While osteal integration, involving bone-to-implant engagement, is an acceptable occurrence, it has certain limitations. The implant, when in functional use, may be subjected to substantial dislocative forces, as, for example, when the patient chews, bites or grinds his teeth, and that force is transmitted directly and in relatively higher magnitudes to the bone. While such forces, when moderate in magnitude, tend to promote bone growth and thus are advantageous, if those forces exceed a predetermined amount, which varies from patient to patient, their effect on the bone is counterproductive, and bone resorption may occur. If this resorption is sufficiently great the implant ultimately becomes loose in the bone and must be removed.

There is another physiological function, in the past inadequately understood, which can occur in connection with the presence of the implant in the bone. That is "fibro-osteal integration", which may be defined at the light microscopic level as an interposition of an peri-implant ligament between well differentiated bone (the implant alveolus) and an implant interface.

The formation of such ligaments is promoted by allowing the implant, after it has been placed in the bone and during the healing process, to experience moderate forces. When the body senses those moderate forces it responds by forming the peri-implant ligament which mitigates, absorbs and redirects those forces. Bone remodeling continually occurs and bone maintenance is achieved. An individual implant surrounded by an optimized peri-implant ligament may maintain its physiologic health under significantly greater functional load than it could when it was only integrated with a direct bone interface. Hence the peri-implant ligament may provide a greater margin of safety and predictability for implant function.

The peri-ligaments structures in question may be considered as performing two functions. The first is to suspend the implant in a sling-like enclosure, thereby to absorb shock and stresses to an appreciable extent so as to protect the bone. In addition, when optimally stressed, the structures may produce bio-electrical which contribute to the stimulation of bone stability and signals growth.

The peri-ligaments are formed by collagen fibers which originate at trabeculae of the implant alveolus and reinsert generally to other trabeculae. Occlusal forces cause tension on the collagen fibers, which, in response, pull on the trabeculae of the implant alveolus into which they are inserted. The resulting bioelectric signal may enhance differentiation and proliferation of osteoblasts, osteoclasts, fibroblasts and other elements that contribute to bone and peri-ligament maintenance associated with the implant interface.

Other basic physiologic benefits are associated with a peri-implant ligament. There are hydraulic effects, brought about by the presence of fluids in the ligament space, and cushioning effects, brought about by the elasticity and compressiblity of the ligament itself. The combined shock absorption effect may be to dampen and significantly reduce the resultant peak occlusal load in bone, and dissipate it over time.

Based on these physiological and biomechanical considerations, it appears evident that the ability of the body to lay down a controlled peri-implant ligament around an endosteal dental implant can be of great benefit.

With these factors in mind we have conducted a very extensive computer-assisted analysis of the relationship between specific implant design factors and the control of concentration of applied stresses as a function of either osteal or fibro-osteal tissue integration. That analysis has led us to conclude that certain design aspects of prior art blade-type implants were in some respects counterproductive and that new design criteria, if met, would produce greatly superior implants suitable for function in either the osteal or fibro-osteal mode of tissue integration. We have discovered that by proper specific design of the implant, optimum advantage can be taken both of osteal and fibro-osteal integration, all in such a way as to improve the degree and longevity of retention of the implant in the bone and to enable that implant to withstand forces greater than it could satisfactorily withstand in the absence of such optimized design.

It is therefore a prime object of the present invention to improve on the design of implants of the type under discussion in order to make them easier to install and to improve the quality and longevity of their functioning.

It is another object of the present invention to specifically design implants to control the stresses to which the patient's bone is subjected and to foster and take optimal advantage of both fibro-osteal and osteal integration.

It is another object of the present invention to provide blade-type implants with removable abutment heads which, when mounted, are sturdily supported, the selection of an appropriately inclined or otherwise configured abutment head permitting the ready adaptation of the implant to the particular requirements of a given patient without requiring bending or distortion.

To the accomplishment thereof, and to such other objects as may hereinafter appear, the present invention relates to the design of dental implants as defined in the appended claims and as described in this specification, taken together with the accompanying drawings, in which:

FIG. 3 is a bottom plan view thereof;

FIG. 4 is a side elevational view thereof;

FIG. 5 is a cross-sectional view taken along the line 5—5 of FIG. 1;

FIG. 7 is a top plan view of the embodiment of FIG. 6;

FIG. 8 is a side elevational view thereof;

FIG. 9 is a cross-sectional view thereof taken along the line 9—9 of FIG. 6;

Figure 13:
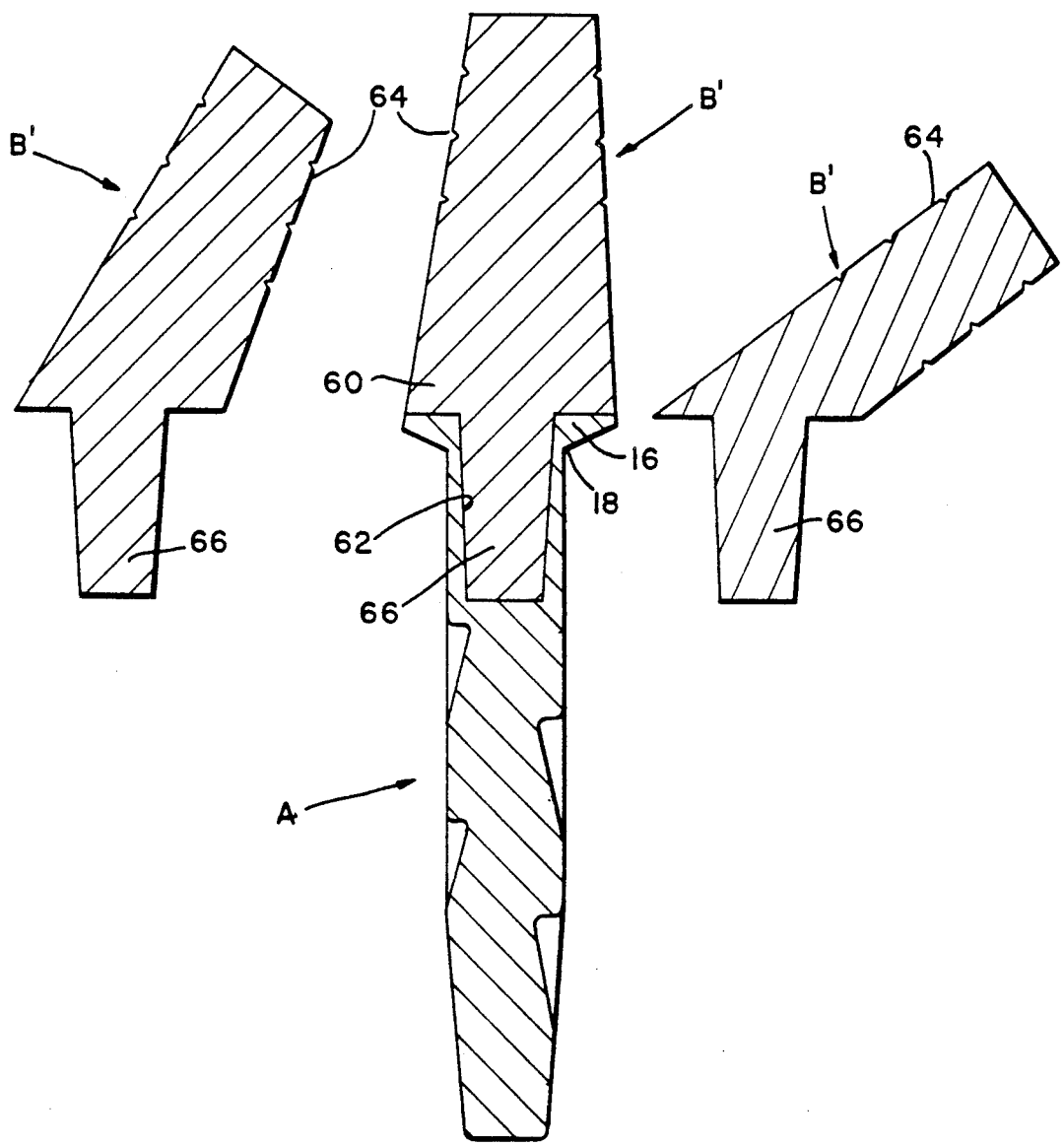
FIG. 13 is a cross-sectional view of the implant of FIG. 11 taken along a line corresponding to the line 5—5 of FIG. 1 and showing three differently inclined removable healing heads.

For purposes of uniformity and clarity of language, the large area surfaces of the implant portion of the present invention will be called front and rear surfaces respectively, the selection of "front" and "rear" being arbitrary, the edge most remote from the head will be called the bottom of the implant, the generally vertically extending edges of the implant portion will be called side edges, and sections of that implant portion extending from side to side across the face thereof will, where appropriate, be referred to as end and intermediate sections, the "intermediate" section being that section located beneath the head and the "end" sections extending laterally out therefrom.

As is well known to those in the field, implants, and particularly blade-type implants, are provided in a wide variety of sizes and shapes depending primarily upon the available bone in the patient's mouth and the nature of the prosthetic device to be supported. Accordingly, it will be understood that the particular implant embodiments here specifically disclosed are but exemplary of the wide variety of designs that may be adopted in accordance with the present invention.

The embodiments of FIGS. 1-5 comprise an implant portion generally designated A which is relatively narrow and deep, from which a single head generally designated B extends upwardly in a position substantially centrally disposed widthwise of the implant. The implant portion A may be considered as comprising an intermediate section generally designated 2 and located beneath the head B, with end sections generally designated 4 and 6 extending laterally therefrom. The end sections 4 and 6 have downwardly inclined upper edges 8, side edges generally designated 10 and bottom edges 12, and the intermediate section 2 has a bottom edge 14 here shown as essentially in line with, and making an uninterrupted connection with, the bottom edges 12 of the end sections 4 and 6 respectively. The upper edges 8 of the end sections 4 and 6 extend inwardly to the head B, which is of considerably greater thickness than the implant portion A, lower edges 16 of the head B preferably being upwardly and outwardly tapered to prevent over-seating of the implant. It will be noted that the upper edges 8 of the end sections 4 and 6 meet the head B at vertices 18, with the side edges 20 of the head B extending up from those vertices 18. As a result the junction between the implant portion A and the head B is devoid of the mesial and distal undercuts that have been characteristic of prior art attachments. Described otherwise, the prior art attachments conventionally have a narrowed neck between the head and the implant portion, but the implants of the present invention preferably do not have any such neck thus substantially increasing the volume of metal available to absorb and physiologically help evenly distribute stress.

The intermediate section 2 of the implant portion A has front and rear surfaces 22 and 24 which, over the major portion of their height, are parallel, the intermediate section 2 therefore being of essentially uniform thickness. Only the very lowermost part of the intermediate section 2, beginning at points 26 on FIG. 5, have front and rear surfaces 28 and 30 which are inclined downwardly toward one another to produce a taper. On the other hand, the end sections 4 and 6 have front and rear surfaces 30 and 32 which are inclined downwardly toward one another so that those sections are downwardly tapered over substantially their entire length. As a result of this disparity in shaping as between the intermediate section 2 on the one hand and the end sections 4 and 6 on the other, the boundary between each end section 4, 6 and the intermediate section 2 is defined by a beveled surface 33 the extent of which increases as the bottom of the implant section is approached. The intermediate section with its large areas of perpendicular surface and greater volume of metal absorbs the highest areas of stress concentration directly beneath the abutment head of the implant, whereas the end sections have large areas of tapered surface with less metal volume, ensuring adequate force distribution to surrounding tissues within physiologic limits of health. Also, the tapering of the end sections assist in adequately and evenly distributing stress on the bone, to achieve the same result.

Grooves 34 are formed in the front and rear surfaces of the implant portion A, with the grooves 34 formed in the front surface preferably being vertically staggered with respect to the grooves 34 formed in the rear surface. While grooving of the implant portion A in prior art implants has been known, the grooves of the implant of the present invention differ from the prior art grooves in several important respects. They are essentially concavely shaped when viewed from the bottom of the implant (in other words, they are inclined downwardly and outwardly from the center of the intermediate section 2) and they are defined by upper surfaces 36 which are generally downwardly facing and preferably substantially horizontal, the remainder of the groove being defined by a downwardly and outwardly inclined surface 38. This materially assists in accommodating downward pressure when the implant is in function. In addition, the depth of the grooves 34 decreases, preferably progressively, as one moves down the implant portion A, thereby to keep the minimum metal thickness of the implant portion sufficiently large. The two lowermost grooves 34 in the embodiment of FIG. 1 extend substantially continuously across the intermediate section 2 and both end sections 4 and 6, crossing ridges constituting portions or continuations of the beveled surface 33, whereas the uppermost groove 34 in each of the end section 4 and 6 are provided in the end sections alone, the corresponding area of the intermediate section being without a corresponding groove portion. This serves to maintain a desired minimum thickness in the implant. The vertical spacing between the grooves on each of the front and rear surfaces of the implant portion A is such that they are separated by appreciable vertical lengths of essentially planar surfaces.

It has been common to provide vents through prior art implants, through which vents bone can grow and, as is now appreciated, peri-implant ligaments of appropriate length can form. Such vents 40 are provided in the implants of the present invention, but, significantly, they are preferably provided only in the end sections 4, 6 and generally not in the intermediate section 2. It will be appreciated that the intermediate section 2 is the section which most directly receives forces exerted on the head B. Because of the vertically staggered location of the grooves 34 on the front and rear surfaces 22 and 24 respectively, a given vent 40, shown in FIG. 1 as being formed in a groove 34, may open onto a non-grooved portion of the rear surface.

The right- and left-hand side surfaces 10 of the implant portion A are provided with notches 42 shaped generally similarly to the grooves 34 by having a substantially horizontal top surface and a downwardly and outwardly inclined side surface. These notches also serve to enhance resistance to downward pressure.

The upper edges 8 of the end sections 4 and 6 are provided with notches 44 preferably extending throughout the thickness thereof to receive shoulder setting tools used to help properly align the implant when it is inserted.

As may perhaps best be seen from FIGS. 4 and 5, representing a symmetical implant, the head B is preferably skewed with respect to the vertical axis of the implant portion A, thus helping to facilitate the solution of parallelism problems, where appropriate, by inserting the implant with its front surface to the rear and minimizing and often avoiding the need to bend the head B relative to the implant portion A.

The implant of FIGS. 6–9 is in many respects similar to that of FIGS. 1–5, and similar reference numerals are used for corresponding structural elements. It has a single head B as in the implant of FIGS. 1–5, but its implant portion A is wider and less deep than that of FIGS. 1–5. Its head B is located considerably off-center widthwise of the implant, so that the end section 6 extends from the intermediate section 2 to a considerably lesser degree than does the end section 4. The bottom edges 12 and 14 are not in line but they do define an essentially continuous bottom edge free of indentations or recesses. In this case the end section 4 is inclined downwardly to a lesser degree than is the end section 6, and the parts of the grooves 34 formed in the end section 4 are correspondingly differently downwardly inclined from the parts of the grooves 34 in the end section 6. This illustrates a generalized design feature of the novel implants of the present invention, according to which the downward inclination of each end section 4 or 6 is inversely related to the degree to which it extends outwardly from the intermediate section.

The off-center location widthwise of the head B permits the implant to be used in a given formed opening in the patient's bone to position the head B more toward the front or the rear depending upon the orientation of the implant, thus providing for flexibility of use to accommodate ideal prosthetic requirements. Since lateral changes in head location are thus provided, the heads B preferably initially extend straight upwardly from the implant portion A, rather than being tilted as in the embodiment of FIGS. 1–5. It will be understood that, for parallelism reasons or otherwise, the heads B of this and other embodiments can readily be bent from their initial position in a direction at right angles to the plane of the implant portion A to accommodate particular installation requirements.

Figure 10:
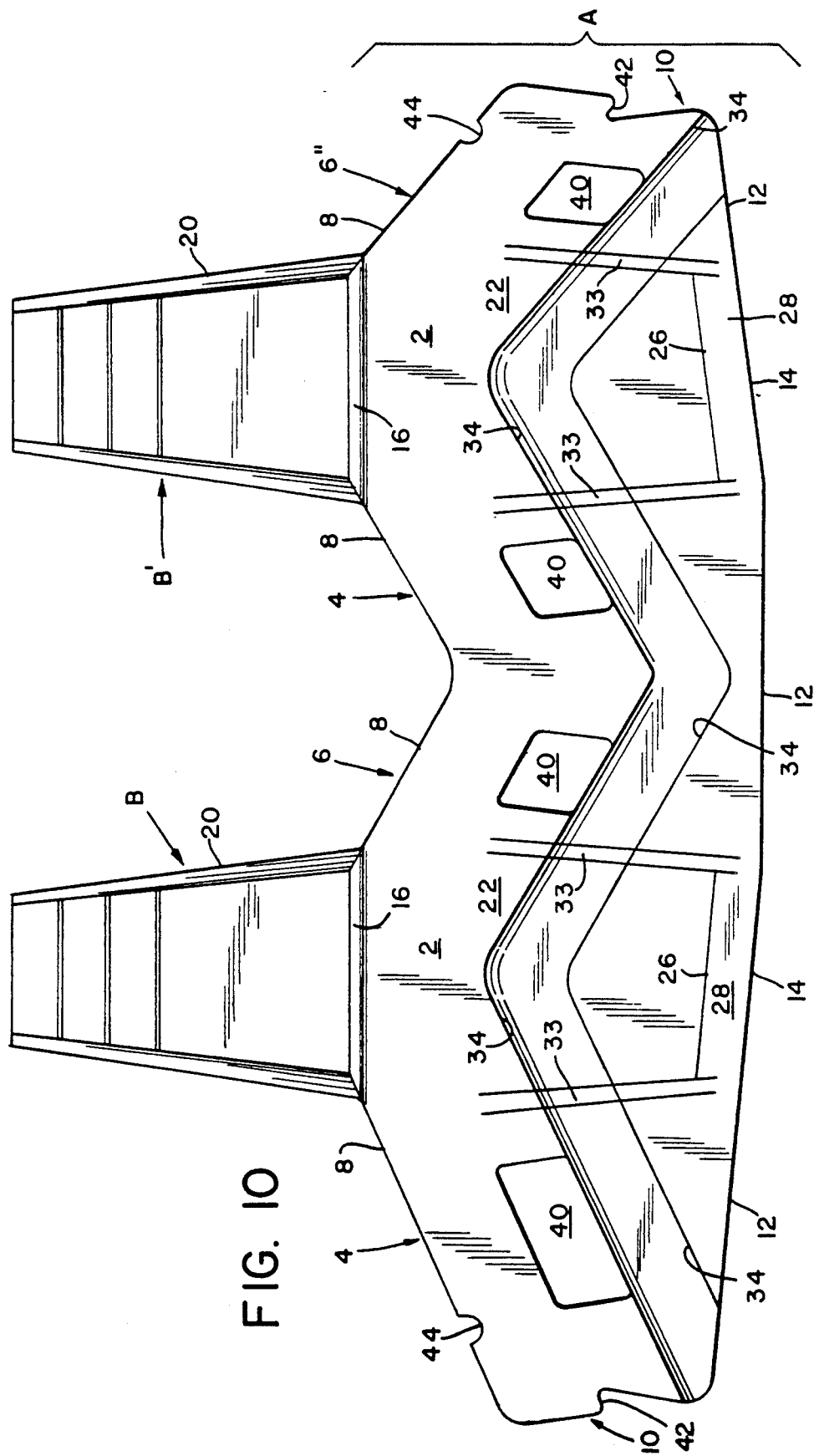
FIG. 10 is a front elevational view of another embodiment of the present invention which has two upwardly extending heads rather than the single head of the other illustrated embodiments.

The embodiment of FIG. 10 also corresponds to and incorporates the novel design features described above, and similar reference numerals are used. It typifies a particularly wide implant provided with a plurality of heads B. The implant portion A has two intermediate sections 2, 2', one beneath each of the heads B, with end sections 4 and 4' extending to the left of the intermediate sections 2 and 2' respectively and with end sections 6 and 6' extending to the right of the intermediate sections 2 and 2' respectively, the end sections 4' and 6 being connected to one another. It will be noted that the end section 4 is longer than the end section 6' and therefore is inclined downwardly to a lesser degree than the end section 6', and that the end sections 4' and 6 are in turn longer than the end section 6' but shorter than the end section 4, and they are therefore inclined downwardly to an intermediate degree when compared to the end sections 4 and 6'. Purely by way of example, the end section 4 may be inclined downwardly by 24° 46', the end sections 4' and 6 are inclined downwardly by 29° 45' and the end section 6' is inclined downwardly by 40° 36'. The grooves 34 formed in each end section are correspondingly downwardly inclined, the grooves 34 formed in each end section are correspondingly downwardly inclined, the grooves 34 formed in the intermediate sections 2 and 2' preferably conforming in inclination on each side to the grooves and inclination characteristic on the respective end sections.

Figure 11:
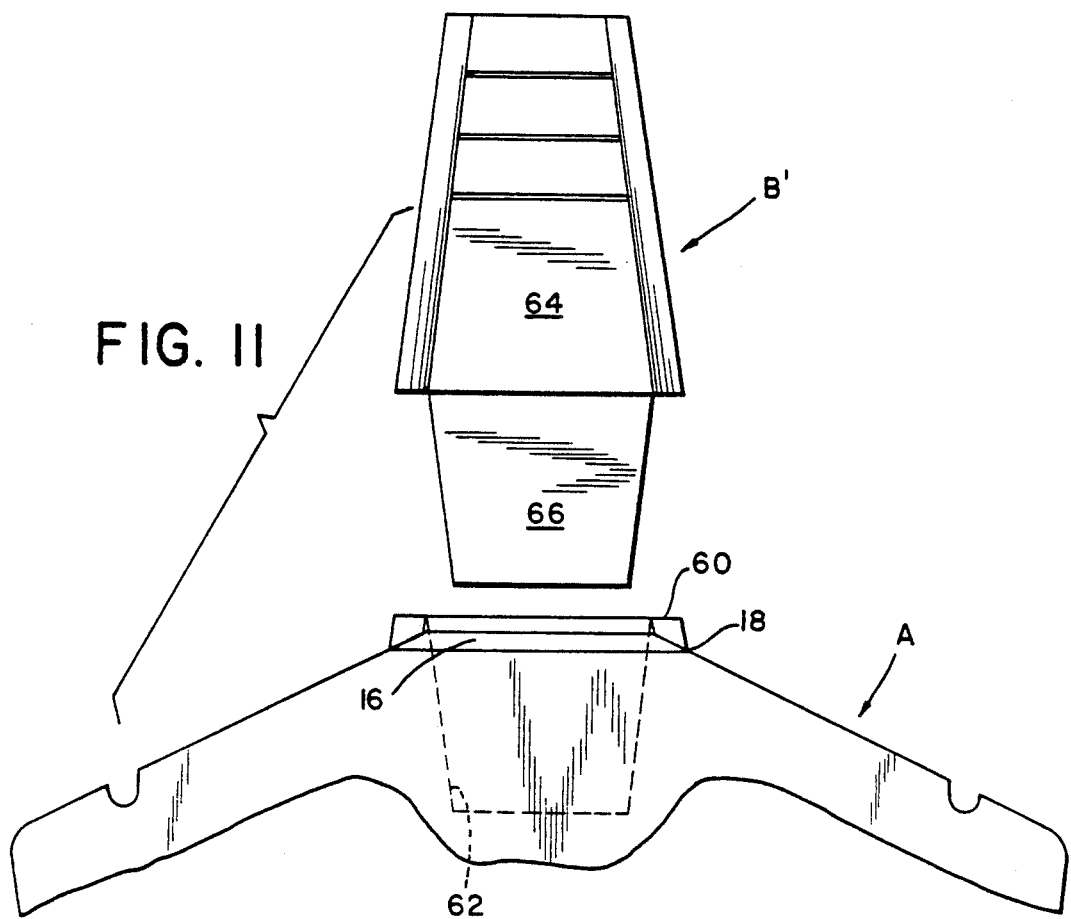
FIG. 11 is an exploded fragmentary front view of an implant of the present invention with a removable healing head.
Figure 12:
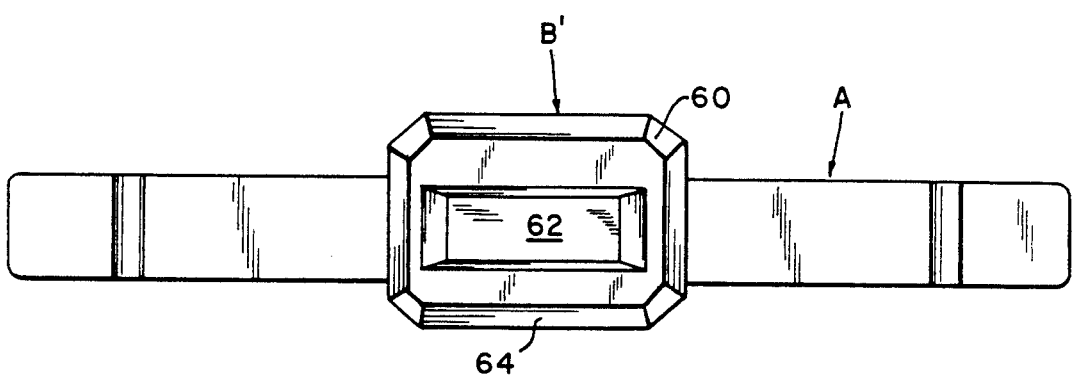
FIG. 12 is a top plan view of the implant of FIG. 11 with the healing head removed.
Figure 1:
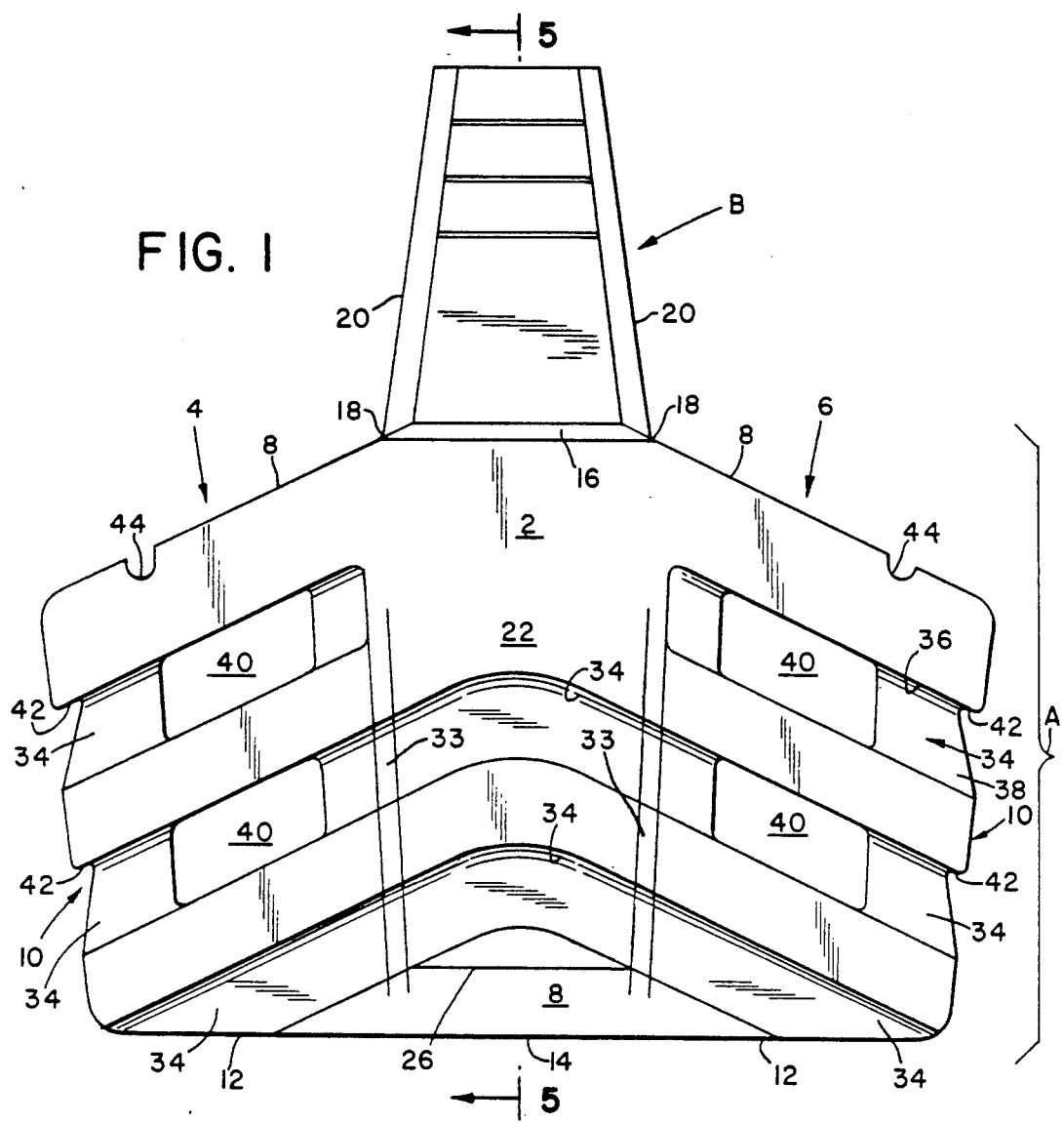
FIG. 1 is a front view of a typical implant of the present invention.
Figure 2:
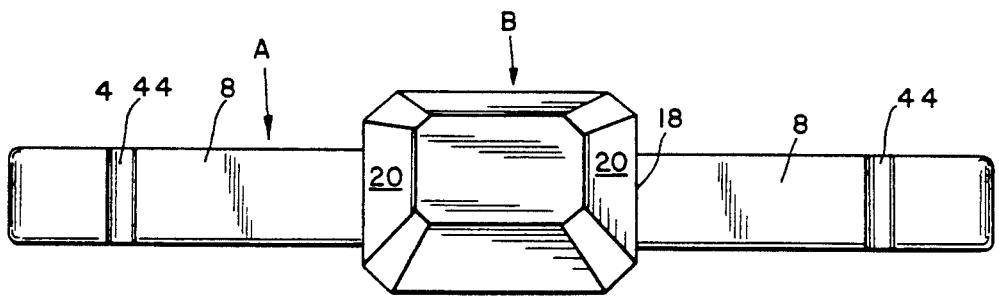
FIG. 2 is a top plan view thereof.
Figure 6:
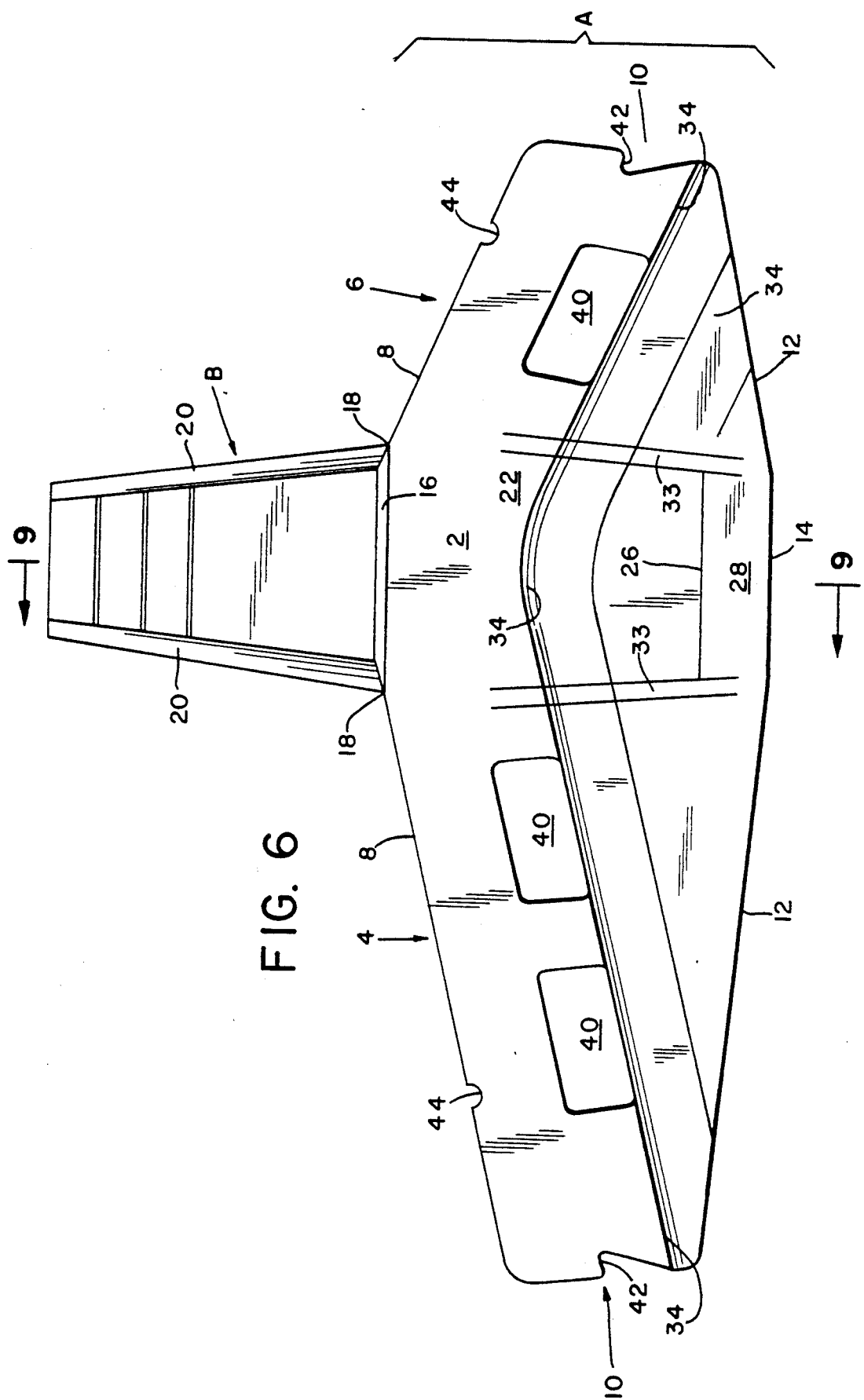
FIG. 6 is a front elevational view of a second embodiment of the present invention in which the end sections extend laterally from the intermediate section to different degrees.

FIGS. 11–13 illustrate a modification of the implant structure to accommodate removable heads, thereby to permit essentially submerging the implant in the gum after it has been inserted to promote healing and osteal integration by minimizing the forces exerted thereon during the healing process. To that end the implant body portion A terminates at upper surface 60 located slightly above the vertices 18 so that the upwardly and outwardly tapered lower edges 16 are present. The surface 60 will be substantially in the form of a long, relatively narrow rectangle. Formed in the body portion 2 and opening onto and extending downwardly from the surface 60 is a relatively deep slot 62 which at the surface 60 defines a long narrow opening spaced inwardly from the periphery of the surface 60 sufficiently to provide adequate structural support for the removable head B. By way of example, the thickness of the implant portion B near its upper surface 60 may be 1.8 mm while the slot 62 at its upper extremity may have a length of 4 mm and a width of 1 mm, thus leaving 0.4 mm of material on either side of the slot 62 in the body of the implant portion B. Vertically, the slot 62 is preferably tapered. The removable head B' comprises a main upstanding portion 64 thicker than the implant body portion A and essentially shaped to correspond to the heads B of the previous embodiments except for their very lowermost portions, from which depends a thin blade-like portion 66 which is shaped correspondingly to the slot 62 in thinness, wideness, taper and, preferably, depth. The depending portion 66 may be a press fit into the slot 62, it may be cemented therein, or it may be then secured in any other fashion. As may be seen from FIG. 13, a plurality of removable heads B' may be provided, each of a somewhat different shape. As disclosed, the upstanding head portions 64 of the three exemplary embodiments disclosed in FIG. 13 are differently axially inclined with respect to their thin depending portions 66, so that when the portions 66 are received within the slots 62 the heads B' will be differently inclined with respect to the implant portion A, thus enabling the implant to be adapted to the particular patient requirements without having to bend the implant, thus obviating a source of failure.

Figure 14:
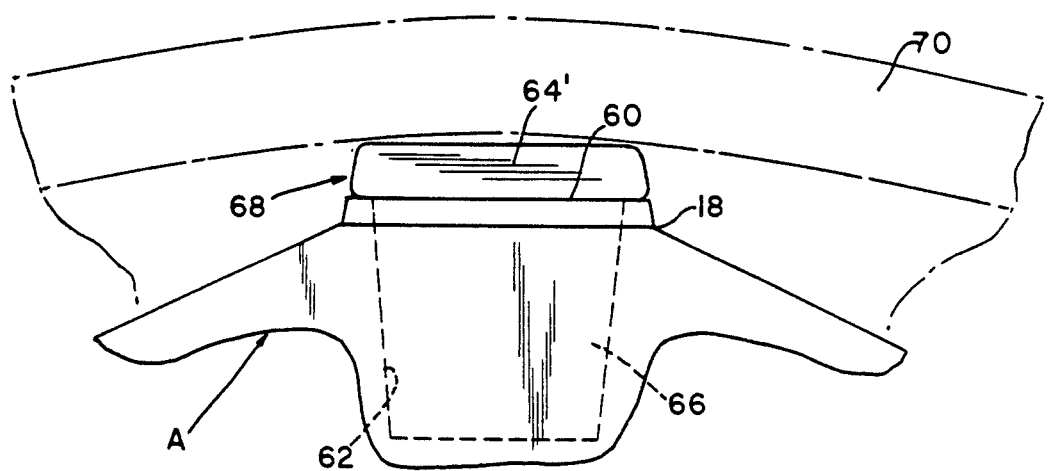
FIG. 14 is a fragmentary front view of an implant of the present invention with a healing head secured thereto, with the location of the gum line during healing being indicated.
Figure 15:
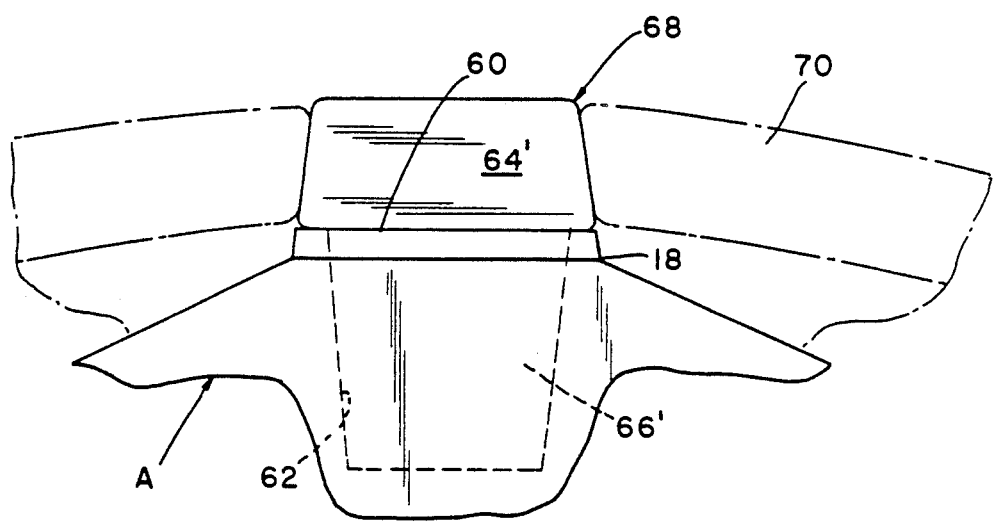
FIG. 15 is a view similar to FIG. 14 but showing a different style of removable healing head.

The use of removable heads B' further permits the implant to be essentially submerged for optimum healing, as has been discussed above. When that is done the slot 62 should not be exposed during the healing period, and hence a healing head 68 is provided, that healing head being composed of a greatly truncated upstanding portion 64' from which the thin blade-like depending portion 66' extends downwardly. As is shown in FIGS. 14 and 15, two types of healing head 68 may be provided for selective use, those heads differing substantially only in the height of their respective upstanding portions 64'. The healing head 68 of FIG. 14 has a very short upstanding portion 64' such that when the implant portion A is inserted into the bone and the healing head 68 is inserted into the implant portion A the upstanding portion 64' will be well below the gum line so that during healing the gum, schematically shown in the drawing and identified by the reference numeral 70, covers the upper surface of the upstanding portion 64'. With the healing head 68 of FIG. 14, after the healing stage and when the abutment head B is to be put into place, it is necessary to surgically separate the gum in order to expose the healing head 68 so that it can be removed and the desired abutment head B inserted. If it is desired to avoid that surgical procedure on the gum, the healing head 68 of FIG. 15 can be used, the upstanding portion 64' of that head being sufficiently high so that when it is put into place in the implant portion A its upper surface extends substantially to the gum line 70. That healing head 68 may then be removed to expose the slot 62 and the selected head B put into place without requiring significant surgical steps.

The various structural features described above have been designed with specific reference to the aforementioned computer-assisted stress analysis and a careful consideration of the physiologic processes which occur. Analysis of the stress contours produced by different design features when subjected to stresses of different magnitudes and directions have resulted in the significant redesign of the implants here disclosed. Thus the downward inclination of the grooves, the shaping of the grooves with downwardly facing upper edges, the elimination of the neck between the implant portion A and the head B, the location of the vents 40, when possible, only in the end sections 4 and 6, the provision of a substantially planar area vertically between the grooves and the formation of the intermediate section 2 with essentially parallel sides over most of its length, which maximize the implant area directly opposed to the patient's bone, the downward tapering of only the end sections 4 and 6, the provision of the notches 42 in the side edges, all have been adopted after determining the distribution and magnitude of stress throughout the implant when subjected to the forces to which it is exposed in use. Stress is, by these features, redistributed in a more homogeneous manner throughout the body of the implant than has been accomplished previously, and much greater resistance to axial loads placed on the implant is provided, which axial loads may constitute 80% to 90% of the total loading of the implant. Additionally, the design provides opportunity for improved mechanical interlock with the biological tissue.

Bearing in mind that too much (hyperfunction) and too little (hypofunction) stress on the bone any place along the interface of the implant may cause bone loss (resorption), the grooves 34 are so positioned and oriented that they spread the stress in a homogeneous manner throughout the implant interface so that the resultant force applied to the bone at each point of the interface is designed to be within the physiologic limits of health (between the parameters of hyper- and hypofunction). The formation of the grooves 34 further increases the flexure of the implant, bringing it closer to that characteristic of the surrounding bone under load, thereby reducing relative motion between the implant interface and surrounding tissue and reducing shear at the implant interface with bone, thus vastly improving physiologic conditions at the interface. The vents 40 are located where stress concentration is lowest and where the stress on the bone would be too low (hypofunction) if the vents were not present. The vents at the same time provide adequate dimensions for biological tissue ingrowth and vascular communication. The substantial planar areas on the front and rear surfaces of the implant which make bone contact produce optimal force absorption in areas of highest stress, and, by distributing forces over an appreciable area, greatly minimize the deleterious effects of both hyperfunction and hypofunction, by predictively helping to control the direction and magnitude of force distribution to be within physiologic limits of health. In addition, those planar areas improve the immobility of the implant during the healing process.

Through the use of a removable head submerged healing is possible, removable healing heads being available to facilitate that healing, and heads of different inclinations or other configurations can be made available so that the optimum head can be selected for a given installation.

While but a limited number of embodiments have been here specifically disclosed, it will be apparent that many variations may be made therein, all within the spirit of the invention as defined in the following claims.

We claim:

1. In a dental implant having an implant portion adapted to be inserted into the bone, the improvement comprising said portion, when viewed from side to side of said implant, comprising end sections and an intermediate section, said end sections being downwardly tapered over at least major portion of their heights, said intermediate portion having substantially parallel front and rear surfaces over a substantial portion of its height.

2. The dental implant of claim 1, in which the lowermost minor fraction of the height of said intermediate portion is downwardly tapered.

3. In a dental implant comprising an implant portion adapted to be inserted into the bone, the improvement comprising said implant portion, when viewed from side to side of said implant, comprising end sections and an intermediate section, said end sections being inclined downwardly from said intermediate section and extending outwardly therefrom to different extents, that end section extending outwardly to the greater extent being inclined downwardly to a lesser extent when compared to the other end portion.

4. In a dental implant comprising an implant portion adapted to be inserted into the bone, the improvement comprising said implant portion, when viewed from side to side of said implant, comprising end sections and an intermediate section, said end sections being inclined downwardly from said intermediate section, said implant portion having grooves in at least one of its front and rear surfaces extending across said end and intermediate portions, said groove lengths formed in said end portions being inclined downwardly to a degree generally corresponding to the degree to which said end sections are inclined downwardly from said intermediate section.

5. In a dental implant comprising an implant portion adapted to be inserted into the bone, the improvement which comprises said implant portion, when viewed from side to side of said implant, comprising end sections and an intermediate section, said implant portion having grooves in at least one of its front and rear surfaces, said end sections being vertically tapered over at least the major portion of their height, said intermediate section having substantially parallel front and rear surfaces over a substantial portion of its height, the front and rear surfaces of the tapered parts of said end sections being joined to the front and rear surfaces of said intermediate section by beveled surfaces.

6. The dental implant of claim 5, in which said grooves are defined in part by an upper generally downwardly facing surface.

7. The dental implant of claim 5, in which said grooves are generally downwardly and outwardly inclined.

8. The dental implant of claim 5, in which said grooves are defined in part by an upper generally downwardly facing surface and in which said grooves are generally downwardly and outwardly inclined.

9. The dental implant of claim 5, in which said grooves near the upper part of said implant section have a greter depth than those near the lower part thereof.

10. The dental implant of claim 5, in which the depth of said grooves progressively decreases from the grooves near the upper part of said implant to the grooves near the lower part thereof.

11. The dental implant of claim 5, in which said grooves are defined in part by an upper generally downwardly facing surface and in which the depth of said grooves progressively decreases from the grooves near the upper part of said implant to the grooves near the lower part thereof.

12. The dental implant of claim 5, in which said grooves are generally downwardly and outwardly inclined and in which the depth of said grooves progressively decreases from the grooves near the upper part of said implant to the grooves near the lower part thereof.

13. The dental implant of claim 5, in which said grooves are defined in part by an upper generally downwardly facing surface, said grooves are generally downwardly and outwardly inclined, and the depth of said grooves progressively decreases from the grooves near the upper part of said implant to the grooves near the lower part thereof.

14. A dental implant having an implant portion adapted to be inserted into the bone, that implant portion, when viewed from side to side of said implant, comprising end sections and an intermediate section, said end sections being downwardly tapered over at least a major portion of their heights, said intermediate section having substantially parallel front and rear surfaces over a substantial portion of its height, grooves in at least one of said front and rear surfaces, which grooves are defined in part by an upper generally downwardly facing surface and being concave when viewed from the bottom of said implant portion, there being a plurality of vertically spaced grooves in at least one of said front and rear surfaces, said grooves nearer the upper part of said implant having a greater depth than grooves nearer the lower part thereof, there being substantially vertical surfaces extending between said grooves in said intermediate section, the front and rear surfaces of the tapered parts of said end sections being joined to the front and rear surfaces of said intermediate section by beveled surfaces.

15. The dental implant of claim 14, in which the lowermost minor fraction of the height of said intermediate section is downwardly tapered.

16. The dental implant of claim 14, in which said end sections extend outwardly from said intermediate section to different extents, that end section extending outwardly to the greater extent being inclined downwardly to a lesser extent when compared to the other end portion and the groove lengths formed in said end portions being inclined downwardly to a degree generally corresponding to the degree to which said end sections are inclined downwardly from said intermediate section.

17. The dental implant of claim 14, in which notches are formed in the end surfaces of said implant portion.

18. In the dental implant of claim 14, a head adapted to extend above the gum and projecting up from said implant portion in line with said intermediate section, and vents extending through said implant portion from front to back, said vents being located in said end sections and said intermediate section being substantially free of said vents.

19. The dental implant of claim 18, in which the lower edge of said implant portion is continuous and substantially without openings or depressions therein.

20. A blade-type implant comprising a thin wide blade-like body portion having an upper surface with a thin wide slot of appreciable depth formed therein, and a removable head, for said implant comprising an upstanding portion thicker than said body portion and having a depending portion shaped correspondingly to said slot in thinness and wideness and adapted to be inserted into and secured in said slot.

21. The blade-type implant of claim 20, in which said body portion is widened substantially only at its uppermost portion alongside only the uppermost portion of said slot, thereby to produce a generally downwardly facing surface near the top of said body portion and additional supporting material along said slot at the top thereof.

22. The blade-type implant of claim 21, in which the lowermost portion of said upstanding portion of said head is of essentially the same shape as said widened uppermost portion of said body portion.

23. The blade-type implant of claim 22, in which the upstanding portion of said head is axially inclined relative to said depending portion.

24. The blade-type implant of claim 22, in which a plurality of heads are provided for selective use with a given body portion, said heads differing in axial inclination of their upstanding portions relative to their depending portions respectively.

25. The blade-type implant of either of claims 20 or 21, in which the upstanding portion of said head is axially inclined relative to said depending portion.

26. The blade-type implant of claim 25, in which a plurality of heads are provided for selective use with a given body portion, said heads differing in axial inclination of their upstanding portions relative to their depending portions respectively.

27. In a dental implant comprising an implant portion adapted to be inserted into the bone, the improvement which comprises said implant portion having a plurality of vertically spaced grooves in at least one of its front and rear surfaces defined in part by an upper generally downwardly facing surface, said grooves nearer the upper part of said implant section having a greater depth than the grooves nearer the lower part thereof.

28. The dental implant of claim 27, in which said grooves are further defined by a side surface generally extending downwardly in an outwardly inclined direction from said upper surface.

29. The dental implant of either of claims 27 or 28, in which the depth of said grooves progressively decreases from the grooves near the upper part of said implant to the grooves near the lower part thereof.

* * * * *